United States Patent [19]

Matson

[11] Patent Number: 4,976,994

[45] Date of Patent: * Dec. 11, 1990

[54] METHOD FOR MODIFYING DIFFUSION SELECTIVITY OF POROUS FRITTED CARBONACEOUS ELECTRODE

[75] Inventor: Wayne R. Matson, Ayer, Mass.

[73] Assignee: ESA, Inc., Bedford, Mass.

[*] Notice: The portion of the term of this patent subsequent to Feb. 14, 2006 has been disclaimed.

[21] Appl. No.: 254,882

[22] Filed: Oct. 7, 1988

Related U.S. Application Data

[63] Continuation of Ser. No. 87,166, Aug. 19, 1987, Pat. No. 4,804,455, which is a continuation of Ser. No. 797,614, Nov. 13, 1985, abandoned.

[51] Int. Cl.$^5$ .............................................. B05D 7/22
[52] U.S. Cl. .................................... 427/230; 204/1 T; 204/411; 204/412; 204/435; 204/294; 204/1.11; 422/70; 436/161
[58] Field of Search ............... 204/1 T, 411, 415, 416, 204/409, 435, 294, 284, 290 R, 291; 422/70; 436/161; 427/230

[56] References Cited

U.S. PATENT DOCUMENTS

| | | | |
|---|---|---|---|
| 3,662,745 | 5/1972 | Cosentino | 204/435 |
| 4,330,387 | 5/1982 | Astruc | 204/294 |
| 4,404,065 | 9/1983 | Matson | 204/1 T |
| 4,507,194 | 3/1985 | Shimomura | 204/435 |
| 4,552,625 | 11/1985 | Van Der Velden | 204/433 |
| 4,563,263 | 1/1986 | Oyama | 204/418 |
| 4,568,442 | 2/1986 | Goldsmith | 204/294 |
| 4,804,455 | 2/1989 | Matson | 204/411 |

Primary Examiner—John F. Niebling
Assistant Examiner—David G. Ryser
Attorney, Agent, or Firm—Hayes, Soloway, Hennessey & Hage

[57] ABSTRACT

The instant invention provides in one aspect porous frit electrodes having improved efficiencies. In another aspect the invention provides inert metal reference and-/or counter electrodes a method of reducing diffusion effects on a metal terminal counter or reference electrode and the electrodes so produced.

2 Claims, 2 Drawing Sheets

FIG. 1A

METHOD FOR MODIFYING DIFFUSION SELECTIVITY OF POROUS FRITTED CARBONACEOUS ELECTRODE

This is a continuation of co-pending application Ser. No. 087,166, now U.S. Pat. No. 4,804,455, filed on Aug. 19, 1987, which is a continuation of Ser. No. 797,614, filed on Nov. 13, 1985, now abandoned.

BACKGROUND OF THE INVENTION

Electrochemical testing systems have become increasingly important in the detection and determination of extremely small concentrations of various electrochemically active species in dilute solution, e.g., in the detection and determination of trace impurities in water, or the detection and determination of trace compounds in biological samples. The invention is particularly useful when electrochemical sensors are used in combination with chromatography and will be described in connection with such utility although other uses are contemplated. Several such systems are described in my earlier U.S. Pat. Nos. 4,404,065, 4,497,199 and 4,511,659, the disclosures of which are incorporated herein by reference.

In such systems, the counter and reference electrodes typically comprise thin solid metallic terminal wires of the like, and the working ("test") electrodes typically comprise porous conductive materials such as fritted carbon or fritted graphite which have a very high surface area to volume ratio to permit effective charge transfer to essentially all of a very small quantity of a particular species of liquid passing adjacent the surface of the working electrode.

The present invention is particularly directed to an improved electrochemical sensor, more specifically for an electrochemical sensor for use with liquid chromatography which provides time separated species in the eluant fluid. A particular embodiment of the invention is specifically directed to a technique for modifying the diffusion rate of transitory species with respect to the counter and/or the reference electrodes. Another embodiment of the invention is specifically directed to a technique for modifying the selectivity of porous working electrodes to make them specific for certain groups of compounds. In such systems the eluant, containing the species to be subject to charge transfer preferably flows through the porous electrode.

BRIEF SUMMARY OF THE INVENTION

The present invention in one aspect is based on the recognition that the normal mechanism of function of terminal wire counter and reference electrodes in a flow cell array is limited by second order effects when a compound of higher concentration develops an earlier oxidation (lower potential) peak in the array, to wit:
1. A transiting shift in the downstream electrode reference potentials caused by products of the high concentration compounds oxidation (reduction) making a transiting reference couple to which the reference electrode responds. The potential shift causes capacitive currents and instability in the base line which limits the sensitivity (decreases the signal to noise ratio) during the time of compound elution; and
2. For certain compounds, a small amount of oxidized (or reduced) material can back react at downstream counter electrodes at the opposite polarity of the test electrode. Depending on the products formed, this can cause small (0.05–0.1%) of the dominant compound peaks at downstream sensors.

In prior art cells, the terminal wire counter and reference electrodes typically are placed in a location in the cell which has been empirically chosen to minimize diffusion effects to these electrodes.

The present invention is based in part on the recognition that:
1. The resolution decreasing effects are transiting; and
2. The effects are related to diffusion limited mechanisms.

Thus, by hindering the ability of a compound to diffuse to the surface of terminal wire reference and/or counter electrodes hindered such that no significant diffusion occurs during the time of passage of the compound through the sensor, undesirable diffusion effects can be decreased.

It also has been recognized that the normal mechanism of function of terminal wire counter and reference electrodes are not diffusion limited. Thus, while a counter electrode may be responding primarily to oxidation (reduction) of the major components of the mobile phase, e.g. $H_2O$, MeOH, at the current requirements that are typical in a sensor, the potentials of the counter electrode are at the beginning of the current wave for the mobile phase and hence are not diffusion limited.

In accordance with one embodiment of the invention terminal wire counter and/or reference electrodes are masked with a permeable membrane that neither inhibits the exchange current on the reference electrode nor the current from the oxidation/reduction of the mobile phase on the counter electrode, but does reduce the diffusion rate of a transitory species.

Another aspect of the invention is based on the observation that the graphite or carbon substrate of a porous frit of the type described as the preferred working electrodes in the above patents has a secondary porosity e.g. on the order of $10^{-6}$–$10^{-7}$ cm., dimensions that typically are equivalent in magnitude to the dimensions of a double layer formed on an electrode during charge transfer. Consequently, material embedded in these pores should present to a reactive species or a double layer structure which is a composite of an embedded material and the electrode substrate material which will change the energy required for charge transfer. Imbedded materials also may present sites for adsorption, sorption or re-orientation of reactive species in close proximity to a conductor that will change the energy required for charge transfer. Thus in accordance with another aspect of the present invention, selected nonelectroactive species (under anticipated sensor conditions) are deposited in the secondary porosity of the working electrode to selectively change the response of a particular species in the eluant to the charge transfer reaction. The resultant working electrode demonstrates considerable change in electrical activity. In one case it may show a significant cathodic shift in the half wave potential for the species to be detected. In another case it may increase the anodic working range over standard sensors when the electrode serves as an anode.

DETAILED DESCRIPTION OF THE INVENTION

In order to more fully understand the present invention, reference should be had to the following detailed description in conjunction with the drawings, wherein like numbers denote like parts, and:

FIG. 1 is an enlarged diagrammatic schematic sectional view of a portion of a porous electrode such as one of electrodes 34a-f in FIG. 1 of my U.S. Pat. No. 4,511,659;

Figure 1:
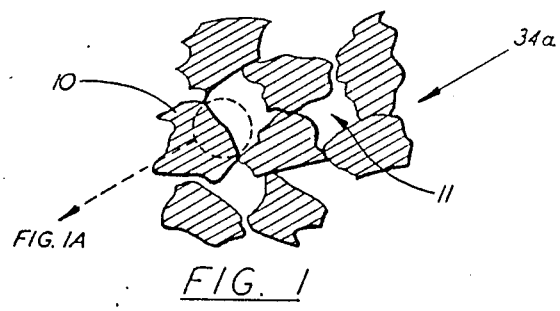
FIG. 1A is a further enlarged portion of FIG. 1.
FIG. 1B is a still further enlargement of a portion of FIG. 1A.
Figure 1A:
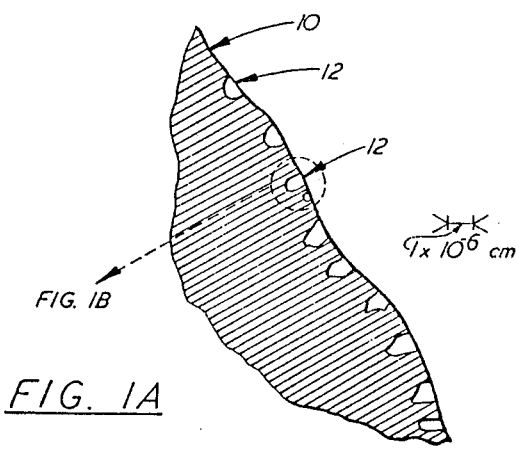
Figure 1B:
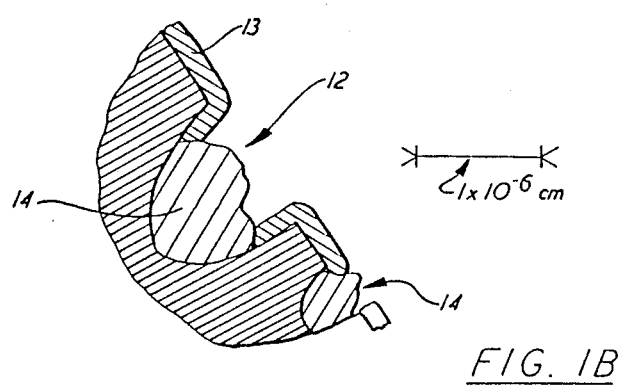
Figure 2:
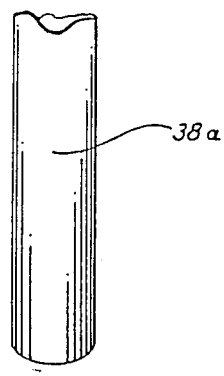
Figure 2A:
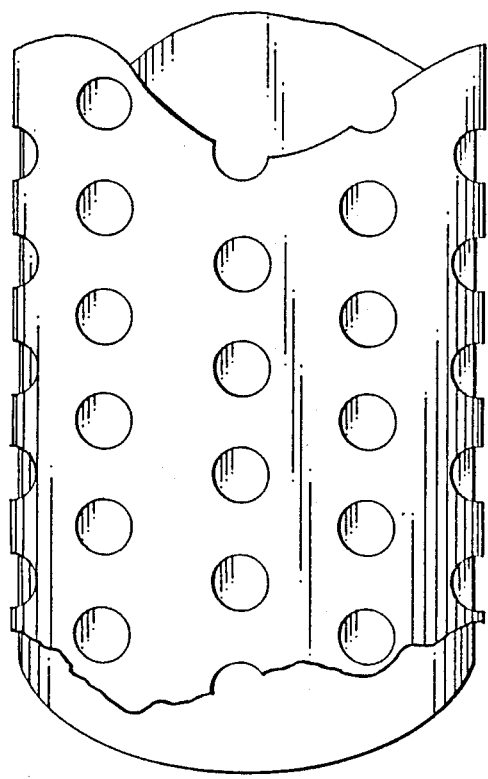

FIG. 2 is an enlarged plan view of a portion of a wire counter or test electrode such as one of the electrodes 44a-f or 50a-f of my U.S. Pat. No. 4,511,659; and FIG. 2A is a further enlarged portion of FIG. 2. This invention will initially be described in conjunction with a modification of a working electrode of the type described in one of the multi electrodes 34a-f shown in FIG. 1 of my U.S. Pat. No. 4,511,659, dated Apr. 16, 1985. This type of electrode, a portion of which is shown at 34a in FIG. 1, comprises a commercially obtainable porous fritted graphite. The primary porosity is indicated at 11 in FIG. 1 and the secondary porosity is shown at 12 in FIGS. 1A and 1B. According to the manufacturer this material has a general pore size distribution as follows:

(a) above $1 \times 10^{-3}$ cm-0% by area of volume
(b) $10^{-4}$–$10^{-5}$ cm-10% by area of volume
(c) below $10^{-6}$ cm-90% by area or volume

EXAMPLE I

This Example shows the modification of the selectivity of porous graphite electrode material in accordance with the present invention.

A piece of fritted graphite having the above-described pore characteristics is impregnated by a mixture of 80% C-48 paraffin and 20% 0.9163-ML density polyethylene containing 1.00 grams per liter sodium salt of naphthalene sulfonic acid at 110° C. and cycling between vacuum and 1000 psi pressure. Electrodes were cut from the impregnated graphited material and these electrodes were treated to remove the impregnating material blocking the frits by heating at 100° C. for 5 minutes under a vacuum of 750-760' mm HgAbs. Thereafter the treated material was rinsed with 50—50 tetrahydrofuran-hexane. The resultant electrode contained approximately 0.01% by weight of sorbed napthalene sulfonic acid and approximately 1% by weight of high molecular weight organic material. The structure of the final product is shown at FIG. 1B where the sorbed napthalene sulfonic acid is indicated at 14 in micropores 12 with some residual organic material indicated at 13.

The frits were assembled in a flow cell detector of a type illustrated in FIG. 1, of my aforesaid U.S. Pat. No. 4,511,659. The treated frits showed a 70 MV cathodic shift in the halfwave potential for norepinephrine, epinephrine and dopamine vs. an untreated carbon frit of similar size used in the identical apparatus under identical potential conditions. Even more significantly, the treated frits showed a 146 MV cathodic shift in the halfwave potential for the octopeptide cholecystokinin 8. The results indicated a possible mechanism based on the attraction of the amine ion moiety of these compounds to the surface of the sensor. The specific data are listed below in Table I:

TABLE I

| (Half Wave Potentials) mV vs. Pd $\alpha$ reference | | |
|---|---|---|
| | Treated Frit | Untreated Frit |
| norepinephrine | 42 | 73 |
| epinephrine | 48 | 88 |

TABLE I-continued

| (Half Wave Potentials) mV vs. Pd $\alpha$ reference | | |
|---|---|---|
| | Treated Frit | Untreated Frit |
| dopamine | 30 | 48 |
| octapeptide | 570 | 716 |

EXAMPLE II

To provide a similar modification of a frit of the above type for anodic use, the frit was treated in the same general manner as in Example I., except that in this case colloidal $Pb(OH)_2$ obtained by precipitating $Pb(NO_3)_2$ with $NH_4OH$ and extracting the colloidal material in the paraffin at 80° C., was substituted for the polyethylene, and mixed with C-48 paraffin as before. This was treated in the same manner, (e.g. vacuum and pressure impregnated) with subsequent vacuum extraction at 100° C. under a vacuum of 750-760 mm HgAbs for 5 minutes. Sensors assembled from the resulting frit showed an increased anodic working range of 360 MV over standard untreated sensors in a 0.1M $Na_2CO_3$ matrix at pH 8, after an initial high anodic current caused by the conversion of $Pb(OH)_2$ to $PbO_2$. The combined effects of the increased anodic range and the changes in the composite electrode structure allowed the direct oxidation of glucose, galactose and sucrose in one test series and the direct oxidation of the amino acids glycine and phenylalinine in another. The specific test data are listed below in Table II:

TABLE II

| (anodic working range) mV vs. $\alpha$ Pd reference | | |
|---|---|---|
| | Treated Frit | Untreated Frit |
| glucose | 1250 | not measurable |
| galactose | 1250 | " |
| sucrose | 1290 | " |
| glycine | 1350 | " |
| phenylalinine | 1380 | " |

Other modifications are feasible; for example, porous fritted carbon or graphite electrodes may be impregnated with metallic mercury, thallium, and/or mercuric chloride dissolved (suspended) in wax, styrene or epoxy monomer. Electrodes so impregnated should provide improved reductive capability for nitrosoamines.

Equally, colloidal nickel oxide (hydroxide) or silver colloid in wax, styrene or monomer, may be used to impregnate the micropores of fritted carbon or graphite electrodes. Electrodes so impregnated should increase the oxidative capability of a sensor electrode containing such precipitated nickel oxide.

Large chain quaternary or ternary amines desorbed in wax, polyethylene, styrene or epoxy monomer may be used to impregnate fritted graphite or carbon electrodes and the resulting electrodes should have increased sensibilities for charge transfer to cationic species.

Other solid organic acids such as dodecyl sulfonic acid and camphor sulfonic acid also may be used in place of the naphthalene sulfonic acid.

EXAMPLE III

This Example shows the modification of the surface of a metal terminal wire electrode in accordance with the present invention.

A palladium wire 38a was coated with cellulose by repetitively alternately dipping the palladium wire in dilute viscose solution (28% solids) and in 1M $H_2SO_4$ to build up a coating of approximately 0.0003" of cellulose.

The wire thus prepared was cut and assembled into in a standard three electrode configuration with coated palladium wire serving as the counter and reference electrodes, and a platinum wire serving as the test electrode in a stirred 200 ml solution of 5M $H_2SO_4$ and 0.5M $H_2SO_4$ to which 1 mM $Fe^{+3}$:1 mM $Fe^{+2}$ was added. The counter electrode was separated from the bulk of the solution in a tube fitted with a porous vycor frit of 0.5 ml such that reaction products could be monitored. An AgAgCl reference electrode also was placed in the solution to measure potentials. Potential of the test electrode was set at +500 mV vs. the coated ("masked") palladium reference electrode. The results are summarized below.

|  | Reference Potential | | | Counter Potential Current | | | |
|---|---|---|---|---|---|---|---|
| Unmasked Reference Electrode | | | | | | | |
| $H_2SO_4$ | 0.071 | 0.066 | 0.074 | −0.11 | −0.11 | −0.11 | 1.0 μa |
| $Fe^{+2}/Fe^{+3}H_2SO_4$ | 0.362 | 0.388 | 0.384 | +0.14 | +0.01 | −0.08 | 15 μa |
| Cellulose Masked Reference Electrode | | | | | | | |
| $H_2SO_4$ | 0.071 | 0.072 | 0.070 | −0.16 | −0.16 | −0.18 | 1.0 μa |
| $Fe^{+2}/Fe^{+3}H_2SO_4$ | 0.069 | 0.078 | 0.198 | −0.23 | −0.26 | −0.21 | 13 μa |

The results showed that the cellulose masking protected the reference electrode from the $Fe^{+2}/Fe^{+3}$ couple overriding the exchange current of the αPdH reaction that forms the initial reference couple, and prevented or decreased the reaction of $Fe^{+3}$ to $Fe^{+2}$ at the counter electrode while sustaining the required current demanded by the reaction at the test electrode.

EXAMPLE IV

Palladium wires were spray coated with Teflon S to build up a coating of approximately 0.0002" thickness. (Teflon S is a trademark of E.I. DuPont de Nemours Company for a synthetic tetrahydrocarbon.) The coated wires thus prepared were dipped sequentially in commercial Teflon etching solution, concentrated $HNO_3/H_2SO_4$ (50:50 by volume) and tetrahydrofuron in a sonifier bath for approximately 1 minute in each. There resulted an etched Teflon coated wire as shown in FIG. 2A.

The Teflon coated/etched palladium wires were cut and assembled as electrodes, and tested in a standard three electrode configuration as in Example III. Similar results to the cellulose masked wires were obtained.

EXAMPLE V

Teflon etched coated wires made in accordance with Example IV were assembled as the counter and reference electrodes 40a-f and 50a-f respectively in a flow cell detector of the type illustrated in FIG. 1 of my aforesaid U.S. Pat. No. 4,511,659 and compared to a standard cell i.e. using base metal palladium reference and counter electrodes of similar size, with respect to resolution of normetaneprine (NMN) From 5-hydroxy indole acetic acid (5HIAA). The particular test compounds were chosen because under a number of conditions, they can co-elute and because 5HIAA shows significant effects of both reference poising and back reaction, and because in work with actual samples using array cells a number of small unidentified peaks also co-elute with 5HIAA at higher potentials.

In the comparison of resolution for the modified and unmodified cells, the following conditions were utilized.

Column: 3 cm Brownlee RP18 5μ guard cartridge
Flow Rate: 1 ml/min
Mobile Phase: 4% MeOH, 200 mg/L octane sulfonic acid, 0.1M $NaH_2PO_4$ adjusted to pH 3.0 with $H_3PO_4$
Detector: Std. cell on modified cell 0.104 D×0.038T (in.) Sensor; 4 cell array high sensitivity electrodes
Potential mV: $T_1(300)$, $T_2(300)$, $T_3300$, $T_4360$, $T_5400$, $T_6440$.

$T_1$ and $T_2$ are at the top of the first 5HIAA oxidation. MN displays is the ratio $T_4$ 1 $T_5$ 18 $T_6$ 1.4.

The efficiencies of the two cells by standard measurement with hydroquinone were determined to be as follows:

|  | T1 | T2 |
|---|---|---|
| Standard | 99.7 | 99.6 |
| Modified | 99.6 | 99.7 |

From the efficiencies of the cells, one could calculate for a mixture of 5HIAA and MNM in a ratio 20 ng to 20 pg of 100/1 the following ratio of currents:

TABLE III

|  | $T_1$ | $T_2$ | $T_3$ | $T_4$ | $T_5$ | $T_6$ |
|---|---|---|---|---|---|---|
| Standard | 997 | 3 | 0.012 | 0.057 | 1 | 0.078 |
| Modified | 996 | 4 | 0.012 | 0/055 | 1 | 0.078 |

The actual data plus or minus S.D. are listed below in Table IV:

|  | $T_1$ | $T_2$ | $T_31$ | $T_4$ | $T_5$ | $T_6$ |
|---|---|---|---|---|---|---|
| Standard | 997 ± 7 | 13 ± 2 | 2 ± 2 | 1.0 ± 1.1 | 1.2 ± 0.8 | 0.1 ± 0.4 |
| Modified | 996 ± 7 | 5 ± 0.8 | 0.03 ± .05 | 0.06 ± .03 | 1.1 ± 0.1 | 0.06 ± 0.03 |

As can be seen from the foregoing, with the standard reference and counter electrode the first effect of reference electrode poising caused an increase in the instability and standard deviation in the upstream electrode measurement and the second effect of reconversion caused a smearing of the resolution of the NMN. With the masked reference and counter electrodes made in accordance with the present invention, the conversion was reduced by a factor of 10 and the precision improved by approximately a factor of 8 on the NMN dominant signal.

Various changes can be made in the above described invention without departing from the spirit and scope thereof, as will be obvious to one skilled in the art.

I claim:

1. A method for modifying the diffusion selectivity of a porous fritted carbonaceous electrode material, said material comprising a frit of individual carbonaceous particles, having a primary porosity before between said individual carbonaceous particles and a secondary porosity within said individual carbonaceous particles comprising depositing within said secondary porosity a non-electroactive material capable of changing the energy required for charge transfer adjacent to the electrode surface.

2. A method according to claim 1 wherein said non-electroactive material is carried in a high molecular weight organic material.

* * * * *

UNITED STATES PATENT AND TRADEMARK OFFICE
CERTIFICATE OF CORRECTION

PATENT NO. : 4,976,994

DATED : December 11, 1990

INVENTOR(S) : MATSON

It is certified that error appears in the above-identified patent and that said Letters Patent is hereby corrected as shown below:

Claim 1, Col. 8, line 5, delete "before".

Signed and Sealed this

Second Day of June, 1992

*Attest:*

DOUGLAS B. COMER

*Attesting Officer*       *Acting Commissioner of Patents and Trademarks*